(12) United States Patent
Hart et al.

(10) Patent No.: US 9,140,649 B2
(45) Date of Patent: Sep. 22, 2015

(54) INFLATABLE MEMBRANE HAVING NON-UNIFORM INFLATION CHARACTERISTIC

(75) Inventors: Douglas P. Hart, Charlestown, MA (US); Federico Frigerio, Chestnut Hill, MA (US); Douglas M. Johnston, Winchester, MA (US); Manas C. Menon, Boston, MA (US); Daniel Vlasic, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 636 days.

(21) Appl. No.: 13/534,476

(22) Filed: Jun. 27, 2012

(65) Prior Publication Data

US 2012/0327426 A1 Dec. 27, 2012

Related U.S. Application Data

(63) Continuation-in-part of application No. 12/508,955, filed on Jul. 24, 2009, now Pat. No. 8,319,184.

(60) Provisional application No. 61/501,600, filed on Jun. 27, 2011, provisional application No. 61/083,394, filed on Jul. 24, 2008, provisional application No. 61/165,708, filed on Apr. 1, 2009.

(51) Int. Cl.
*G01T 1/20* (2006.01)
*G01N 21/64* (2006.01)
(Continued)

(52) U.S. Cl.
CPC ........ *G01N 21/6456* (2013.01); *A61B 1/00082* (2013.01); *A61B 1/043* (2013.01); *A61B 1/227* (2013.01); *A61B 5/1077* (2013.01); *A61B 5/1079* (2013.01); *G01B 11/0658* (2013.01); *G01B 11/24* (2013.01); *A61B 1/015* (2013.01); *A61B 1/018* (2013.01); *A61B 1/2736* (2013.01); *A61B 5/1076* (2013.01); *A61B 5/6817* (2013.01); *G01N 2021/6421* (2013.01);
(Continued)

(58) Field of Classification Search
CPC ........................................................ G01B 11/24
USPC .............................. 356/601; 348/46; 340/540
See application file for complete search history.

(56) References Cited

U.S. PATENT DOCUMENTS 2,780,129 A 2/1957 Wood
4,150,341 A 4/1979 Ferguson
(Continued)

FOREIGN PATENT DOCUMENTS

CN 1556914 A 2/2002
EP 2178012 4/2010
(Continued)

OTHER PUBLICATIONS

"U.S. Appl. No. 13/534,932 Notice of Publication", U.S. Appl. No. 13/534,932 No. Publ_122712 NPL-30 Dec. 27, 2012, 1.
(Continued)

*Primary Examiner* — David Porta
*Assistant Examiner* — Meenakshi Sahu
(74) *Attorney, Agent, or Firm* — Strategic Patents, P.C.

(57) ABSTRACT

Various improvements to inflatable membranes are disclosed. These improvements include techniques for advantageously controlling the inflation of a membrane within a cavity, such as a human ear canal.

19 Claims, 5 Drawing Sheets

(51) Int. Cl.
*A61B 1/04* (2006.01)
*A61B 1/227* (2006.01)
*G01B 11/06* (2006.01)
*G01B 11/24* (2006.01)
*A61B 1/00* (2006.01)
*A61B 1/015* (2006.01)
*A61B 1/018* (2006.01)
*A61B 1/273* (2006.01)
*A61B 5/107* (2006.01)
*A61B 5/00* (2006.01)

(52) U.S. Cl.
CPC ............... *G01N 2021/6439* (2013.01); *G01N 2021/6491* (2013.01); *G01N 2201/0221* (2013.01)

(56) References Cited

U.S. PATENT DOCUMENTS

| | | | | |
|---|---|---|---|---|
| 4,244,377 | A | * | 1/1981 | Grams ............... 600/555 |
| 4,841,156 | A | | 6/1989 | May et al. |
| 4,950,227 | A | | 8/1990 | Savin et al. |
| 5,474,542 | A | | 12/1995 | Gandi et al. |
| 5,619,330 | A | | 4/1997 | Ehemann, Jr. et al. |
| 5,634,937 | A | | 6/1997 | Mollenauer et al. |
| 5,717,217 | A | | 2/1998 | Neckers et al. |
| 5,904,651 | A | * | 5/1999 | Swanson et al. ............ 600/407 |
| 5,931,789 | A | | 8/1999 | Alfano et al. |
| 6,081,577 | A | | 6/2000 | Webber |
| 6,319,242 | B1 | | 11/2001 | Patterson et al. |
| 6,339,648 | B1 | * | 1/2002 | McIntosh et al. ............ 381/328 |
| 6,440,102 | B1 | * | 8/2002 | Arenberg et al. ............ 604/96.01 |
| 6,533,062 | B1 | | 3/2003 | Widmer et al. |
| 6,566,024 | B1 | | 5/2003 | Bourdelais et al. |
| 6,621,951 | B1 | | 9/2003 | Zhao et al. |
| 6,751,494 | B2 | | 6/2004 | Collier et al. |
| 7,286,242 | B2 | | 10/2007 | Kim et al. |
| 7,555,356 | B2 | | 6/2009 | Roth et al. |
| 7,606,381 | B2 | | 10/2009 | Haussmann |
| 7,803,634 | B2 | | 9/2010 | Klimov et al. |
| 7,846,390 | B2 | | 12/2010 | Hegazi |
| 7,858,953 | B2 | | 12/2010 | Hughes et al. |
| 8,107,086 | B2 | | 1/2012 | Hart et al. |
| 8,112,146 | B2 | | 2/2012 | Hart et al. |
| 8,116,853 | B2 | | 2/2012 | Hart et al. |
| 8,116,854 | B2 | | 2/2012 | Hart et al. |
| 8,310,560 | B2 | | 11/2012 | Hart et al. |
| 8,384,916 | B2 | | 2/2013 | Hart et al. |
| 8,493,574 | B2 | | 7/2013 | Hart et al. |
| 8,619,154 | B2 | | 12/2013 | Hart et al. |
| 8,845,526 | B2 | * | 9/2014 | Hart et al. ............ 600/200 |
| 2002/0158873 | A1 | | 10/2002 | Williamson |
| 2003/0171652 | A1 | | 9/2003 | Yokoi et al. |
| 2004/0022684 | A1 | | 2/2004 | Heinze et al. |
| 2004/0112978 | A1 | | 6/2004 | Reichel et al. |
| 2004/0208350 | A1 | | 10/2004 | Rea et al. |
| 2004/0253824 | A1 | | 12/2004 | Tegeder |
| 2005/0088435 | A1 | | 4/2005 | Geng |
| 2005/0202363 | A1 | | 9/2005 | Osterwalder |
| 2006/0079924 | A1 | | 4/2006 | Sanders et al. |
| 2006/0173637 | A1 | | 8/2006 | Martin |
| 2007/0127756 | A1 | | 6/2007 | Slabaugh et al. |
| 2007/0244371 | A1 | | 10/2007 | Nguyen et al. |
| 2008/0009746 | A1 | | 1/2008 | Forster |
| 2008/0033275 | A1 | | 2/2008 | Blank |
| 2008/0068619 | A1 | | 3/2008 | Vial et al. |
| 2008/0169044 | A1 | | 7/2008 | Osborne et al. |
| 2009/0238374 | A1 | * | 9/2009 | Keady ............ 381/72 |
| 2009/0296980 | A1 | | 12/2009 | Yi |
| 2010/0019170 | A1 | | 1/2010 | Hart et al. |
| 2010/0020070 | A1 | | 1/2010 | Hart et al. |
| 2010/0022893 | A1 | | 1/2010 | Hart |
| 2010/0027014 | A1 | | 2/2010 | Hart et al. |
| 2010/0039534 | A1 | | 2/2010 | Hart et al. |
| 2010/0042002 | A1 | | 2/2010 | Hart et al. |
| 2010/0065793 | A1 | | 3/2010 | Hart et al. |
| 2010/0067756 | A1 | | 3/2010 | Hart et al. |
| 2011/0290005 | A1 | | 12/2011 | Hart et al. |
| 2012/0327427 | A1 | * | 12/2012 | Hart et al. ............ 356/601 |
| 2013/0002426 | A1 | * | 1/2013 | Hart et al. ............ 340/540 |
| 2013/0002824 | A1 | | 1/2013 | Hart et al. |
| 2013/0003078 | A1 | * | 1/2013 | Hart et al. ............ 356/601 |

FOREIGN PATENT DOCUMENTS

| | | |
|---|---|---|
| JP | 2003-75126 | 3/2003 |
| JP | 2003075126 | 3/2003 |
| WO | WO-03025497 | 3/2003 |
| WO | WO-2010/011938 A1 | 1/2010 |
| WO | WO2013003416 A2 | 1/2013 |

OTHER PUBLICATIONS

"U.S. Appl. No. 13/534,549, Non-Final Office Action mailed Mar. 20, 2015", 24 pages.

"U.S. Appl. No. 13/534,818, Non Final Office Action mailed Apr. 9, 2015", 41 pages.

"U.S. Appl. No. 13/534,932, Non-Final Office Action mailed Apr. 16, 2015", 34 pages.

European Patent Office, "EP Application Serial No. 12804563.0, EP Supplemental Search Report dated Apr. 24, 2015", 7 pages.

"U.S. Appl. No. 13/534,892, Notice of Allowance mailed May 23, 2014", 21 pages.

"International Application Serial No. PCT/US12/044325, Preliminary Report on Patenability mailed Apr. 10, 2014", 11 pages.

Prasciolu, M et al., "Three-dimensional digital scanner based on micromachined micromirror for the metrological measurement of the human ear canal", J. Vac. Sci. Technol B. vol. 23, No. 6, Nov./Dec. 2005 , 2990-2994.

"U.S. Appl. No. 12/508,804, Notice of Allowance mailed Sep. 27, 2011", U.S. Appl. No. 12/508,804—NoA NPL-12 Sep. 27, 2011, 14 pgs.

"U.S. Appl. No. 12/508,955, Notice of Allowance mailed Sep. 12, 2012", U.S. Appl. No. 12/508,955—NoA NPL-23 Sep. 12, 2012, 18 pages.

"U.S. Appl. No. 12/508,804, Non Final Office Action mailed Jul. 25, 2011", U.S. Appl. No. 12/508,804—NFOA NPL-11 Jul. 25, 2011, 15 pages.

"Appl. U.S. Appl. No. 12/508,866, Non-Final Office Action mailed Jul. 19, 2011", U.S. Appl. No. 12/508,866—NFOA NPL-10 Jul. 19, 2011, 13 pages.

"U.S. Appl. No. 12/508,866, Final Office Action mailed May 18, 2011", U.S. Appl. No. 12/508,866—FOA NPL-9 May 18, 2011, 21 pages.

"U.S. Appl. No. 12/508,955, Non-Final Office Action mailed Mar. 16, 2012", U.S. Appl. No. 12/508,955-NFOA NPL-25 Mar. 16, 2012, 28 pages.

Pirzanski, Chester, "Earmolds and Hearing Aid Shells: A Tutorial Part 2: Impression-Taking Techniques that Result in Fewer Remakes", May 2006 the Hearing review Mar. 11, 2011, 1-7.

Hidrovo, C et al., ""Dual Emission Laser Induced Fluorescence Technique (DELIF) for Oil Film Thickness and Temperature Measurement"", AMSE/JSME Fluids Engineering Decision Summer Meeting Jul. 23-28, 2000 Boston, MA 2000, 1-8.

"Application Serial No. 200980128849.4—Chinese—First Office Action", SN:CN200980128849-4_Chinese NPL-19 Feb. 21, 2012, pp. 1-6.

"Application Serial No. 200980128849.4—English—First Office Action", SN:CN200980128849-4_English NPL-18 Feb. 21, 2012, pp. 1-12.

"Appl. China SN: CN1556914 English Abstract", SN:CN1556914 NPL-20 Dec. 22, 2004, 1 page.

"U.S. Appl. No. 12/508,866, Notice of Allowance mailed Dec. 21, 2011", U.S. Appl. No. 12/508,866—NoA NPL-14 Dec. 21, 2011, 13 pgs.

"International Application Serial No. PCT/US09/51710, Search Report and Written Opinion mailed Nov. 19, 2009", PCTUS0951710-SR NPL-6 Nov. 19, 2009, 15 Pgs.

(56) References Cited

OTHER PUBLICATIONS

"U.S. Appl. No. 12/509,091, Notice of Allowance mailed Nov. 15, 2011", U.S. Appl. No. 12/509,091—NoA NPL-15 Nov. 15, 2011, 16 pgs.

"U.S. Appl. No. 12/508,991, Notice of Allowance mailed Nov. 14, 2011", U.S. Appl. No. 12/508,991—NoA NPL-16 Nov. 14, 2011, 6 Pgs.

"U.S. Appl. No. 12/508,991, Non-Final Office Action mailed Oct. 13, 2011", U.S. Appl. No. 12/508,991—NFOA NPL-13 Oct. 13, 2011, 14 Pgs.

"U.S. Appl. No. 12/508,866, Non-Final Office Action mailed Jan. 31, 2011", U.S. Appl. No. 12/508,866—NFOA NPL-7 Jan. 31, 2011, all pages.

"U.S. Appl. No. 12/508,911, Non-Final Office Action mailed Jan. 30, 2012", U.S. Appl. No. 12/508,911-NFOA NPL-17 Jan. 30, 2012, 22 pages.

Hidrovo, C. et al., ""2-D Thickness and Temperature Mapping of Fluids by Means of a Two Dye Laser Induced Fluorescence Ratiometric Scheme"", Journal of Flow Visualization and Image Processing vol. 9, Issue 2 Jun. 2002, 171-191.

Hidrovo, C. et al., ""Excitation Non-Linearities in Emission Reabsorption Laser Induced Fluorescence (ERLIF) Techniques"", Journal of Applied Optics vol. 43, No. 4 Feb. 2004, 894-913.

Hidrovo, Carlos H. et al., "Emission reabsorption laser induced fluorescence (EELIF) film thicknessmeasurement", Department of Mecbanical Engineering, Measurement and Science Technology, Massachusetts Institute of Technology, Cambridge, MA 02139-4307, USA vol. 12 Jan. 15, 2001, pp. 467-477.

"International Application U.S. Appl. No. PCT/US20121044325, Search Report and Written Opinion mailed Sep. 14, 2012", PCTUS20121044325-SR NPL-26 Sep. 14, 2012, 6 pages.

* cited by examiner

INFLATABLE MEMBRANE HAVING NON-UNIFORM INFLATION CHARACTERISTIC

CROSS-REFERENCE TO RELATED APPLICATIONS

This application claims the benefit of U.S. Prov. App. No. 61/501,600 filed on Jun. 27, 2011. This application is also a continuation-in-part of U.S. application Ser. No. 12/508,955, filed on Jul. 24, 2009, which application claims the benefit of U.S. Provisional Patent Application No. 61/083,394 filed on Jul. 24, 2008 and U.S. Provisional Patent Application No. 61/165,708 filed on Apr. 1, 2009. Each of the foregoing applications is incorporated herein by reference in its entirety.

FIELD OF INVENTION

This document relates to inflatable membranes having non-uniform inflation characteristics.

BACKGROUND

Techniques have been disclosed for capturing thickness measurements inside an inflated membrane, as described for example in commonly-owned U.S. Pat. No. 8,107,086 and reconstructing three-dimensional images from these measurements.

While these techniques are generally useful for measuring interior cavities, there remains a need for improved inflatable membranes adapted to capturing such data in particular environments such as within a human ear canal.

SUMMARY

Various improvements to inflatable membranes are disclosed for use in three-dimensional imaging of interior spaces based upon distance measurements. These techniques may be used alone or in combination for improved data capture.

In one aspect, a device disclosed herein includes an inflatable membrane having a proximal end with an opening, a distal end, and an interior accessible through the opening, wherein the inflatable membrane has an inflation characteristic that is non-uniform, thereby causing the membrane to inflate in a predetermined manner; a supply of a medium coupled to the interior through the opening; and a three-dimensional scanning system including at least one scanner element disposed within the interior to capture data from the interior and a processor programmed to calculate a three-dimensional shape of the interior based upon the data.

The device may include a pump configured to controllably deliver the medium into the interior. The pump may be configured to deliver the medium at a controlled pressure. The device may include an illumination source disposed within the interior and positioned to illuminate a surface of the interior. The three-dimensional scanning system may calculate a distance through the medium to a point on the interior using a ratio of two different wavelengths of light. The medium may selectively absorbs one wavelength of light more than another wavelength of light. The medium may include at least one of a liquid, a gas, and a gel. The inflatable membrane may have a gross geometry corresponding to a human ear canal. The inflatable membrane may have a gross geometry corresponding to human anatomy selected from a group consisting of a stomach, an esophagus, and a bladder. The predetermined manner of inflation may include inflation at the distal end before inflation at the proximal end. The inflation characteristic may include a thickness of the inflatable membrane. The inflation characteristic may include a hardness of the inflatable membrane. The device may include a reinforcing sheath about a portion of the inflatable membrane to impart the non-uniform inflation characteristic to the inflatable membrane. The sheath may be disposed near the proximal end of the inflatable membrane. The inflation characteristic may include a pattern of relatively inelastic material disposed on a portion of the inflatable membrane. The inflation characteristic may include a bellows formed into a portion of the inflatable membrane. A portion of the inflatable membrane may be exercised prior to use to alter an elasticity of the portion, thereby imparting the inflation characteristic to the inflatable membrane. The inflatable membrane may have an oval cross section. The inflatable membrane may have a circular cross section. The inflatable membrane may be formed of an elastic material.

In another aspect, disclosed herein is a device including an inflatable membrane having a proximal end with an opening, a distal end, and an interior accessible through the opening, wherein the inflatable membrane has one or more fiducials on the interior; a supply of a medium coupled to the interior through the opening; and a three-dimensional scanning system including at least one scanner element disposed within the interior to capture data from the interior and a processor programmed to calculate a three-dimensional shape of the interior based upon the data, wherein the processor uses the one or more fiducials to calculate the three-dimensional shape.

The device may include a pump configured to controllably deliver the medium into the interior. The pump may be configured to deliver the medium at a controlled pressure. The device may include an illumination source disposed within the interior and positioned to illuminate a surface of the interior. The three-dimensional scanning system may calculate a distance through the medium to a point on the interior using a ratio of two different wavelengths of light. The medium may selectively absorb one wavelength of light more than another wavelength of light. The medium may include at least one of a liquid, a gas, and a gel. The one or more fiducials may be used to register multiple frames of image data acquired from the at least one scanner element. The one or more fiducials may include predetermined patterns printed on the interior. The one or more fiducials may include predetermined patterns embedded in a material of the inflatable membrane. The one or more fiducials may include predetermined three-dimensional shapes on the interior of the inflatable membrane.

In another aspect, a device disclosed herein includes an inflatable membrane having a proximal end with an opening, a distal end, and an interior accessible through the opening, wherein the inflatable membrane may includes an optical coating on the interior; a supply of a medium coupled to the interior through the opening; and a three-dimensional scanning system including at least one scanner element disposed within the interior to capture data from the interior and a processor programmed to calculate a three-dimensional shape of the interior based upon the data, wherein the optical coating may be selected to improve performance of the three-dimensional scanning system.

The optical coating may include a matte finish. The optical coating may include a fluorescent dye. The optical coating may include an optically absorptive coating. The optical coating may include a predetermined color.

In another aspect, the device disclosed herein includes an inflatable membrane having a proximal end with an opening, a distal end, and an interior accessible through the opening, wherein the inflatable membrane may include an optical material disposed within a wall of the inflatable membrane; a supply of a medium coupled to the interior through the opening; and a three-dimensional scanning system including at least one scanner element disposed within the interior to capture data from the interior and a processor programmed to calculate a three-dimensional shape of the interior based upon the data, wherein the optical material may be selected to improve performance of the three-dimensional scanning system.

The optical material may include a fluorescent dye or a luminescent material. The optical material may include a black pigment. The optical material may be disposed in a pattern to form one or more fiducials for the three-dimensional scanning system.

In another aspect, a device disclosed herein includes an inflatable membrane having a proximal end with an opening, a distal end, and an interior accessible through the opening; a supply of a medium coupled to the interior through the opening; a proximity sensor configured to provide a signal indicative of a proximity of the distal end to an external object; and a three-dimensional scanning system including at least one scanner element disposed within the interior to capture data from the interior and a processor programmed to calculate a three-dimensional shape of the interior based upon the data, wherein the processor may be further programmed to receive the signal from the proximity sensor and generate an alert under one or more predetermined conditions.

The device may include a pump configured to controllably deliver the medium into the interior. The pump may be configured to deliver the medium at a controlled pressure. The device may include an illumination source disposed within the interior and positioned to illuminate a surface of the interior. The three-dimensional scanning system may calculate a distance through the medium to a point on the interior using a ratio of two different wavelengths of light. The medium may selectively absorb one wavelength of light more than another wavelength of light. The medium may include at least one of a liquid, a gas, and a gel. The alert may activate an audible alarm. The alert may activate a visual alarm. The alert may activate a tactile alarm. The proximity sensor may be disposed in the interior of the inflatable membrane. The proximity sensor may be disposed on an exterior of the inflatable membrane. The proximity sensor may include an ultrasound transducer.

In another aspect, a device disclosed herein includes an inflatable membrane having a proximal end with an opening, a distal end, and an interior accessible through the opening; a supply of a medium coupled to the interior through the opening; and a three-dimensional scanning system including one or more optical sensors disposed within the interior to capture image data from the interior and a processor programmed to calculate a three-dimensional shape of the interior based upon the data, wherein the one or more optical sensors include a coating having a first index of refraction matched to a second index of refraction of the medium.

The device may include a pump configured to controllably deliver the medium into the interior. The pump may be configured to deliver the medium at a controlled pressure. The device may include an illumination source disposed within the interior and positioned to illuminate a surface of the interior. The three-dimensional scanning system may calculate a distance through the medium to a point on the interior using a ratio of two different wavelengths of light. The medium may selectively absorb one wavelength of light more than another wavelength of light. The medium may include at least one of a liquid, a gas, and a gel.

In another aspect, a device disclosed herein includes an inflatable membrane having a proximal end with an opening, a distal end, and an interior accessible through the opening; a window of transparent material in the distal end providing a view from the interior of the inflatable membrane to an exterior of the inflatable membrane; a supply of a medium coupled to the interior through the opening; and a three-dimensional scanning system including one or more scanner elements disposed within the interior to capture data from the interior and a processor programmed to calculate a three-dimensional shape of the interior based upon the data, at least one of the one or more scanner elements including a camera oriented toward the window.

The device may include a pump configured to controllably deliver the medium into the interior. The pump may be configured to deliver the medium at a controlled pressure. The device may include an illumination source disposed within the interior and positioned to illuminate a surface of the interior. The three-dimensional scanning system may calculate a distance through the medium to a point on the interior using a ratio of two different wavelengths of light. The medium may selectively absorb one wavelength of light more than another wavelength of light. The medium may include at least one of a liquid, a gas, and a gel. The device may include a display coupled to the camera and configured to display video images from the camera. The device may include an optical coating on the camera having a first index of refraction matched to a second index of refraction of the medium. The device may include a proximity sensor configured to provide a signal indicative of a proximity of the distal end to an external object.

In another aspect, a device disclosed herein includes an inflatable membrane having a proximal end with an opening, a distal end, and an interior accessible through the opening; a window of transparent material in the distal end providing a view from the interior of the inflatable membrane to an exterior of the inflatable membrane; a fixture in the interior of the inflatable membrane shaped and sized to receive an imaging device and to align the imaging device to the window to provide a view of the exterior through the window with the imaging device; a supply of a medium coupled to the interior through the opening; and a three-dimensional scanning system including one or more scanner elements disposed within the interior to capture data from the interior and a processor programmed to calculate a three-dimensional shape of the interior based upon the data.

The device may include a pump configured to controllably deliver the medium into the interior. The pump may be configured to deliver the medium at a controlled pressure. The device may include an illumination source disposed within the interior and positioned to illuminate a surface of the interior. The three-dimensional scanning system may calculate a distance through the medium to a point on the interior using a ratio of two different wavelengths of light. The one or more scanner elements may include the imaging device. The medium may include at least one of a liquid, a gas, and a gel. The device may include a display coupled to the imaging device and configured to display video images from the imaging device. The imaging device may have a lens with an optical coating having a first index of refraction matched to a second index of refraction of the medium. The device may include a proximity sensor configured to provide a signal indicative of a proximity of the distal end to an external object.

In another aspect, a device disclosed herein includes an inflatable membrane having a proximal end with an opening, a distal end, and an interior accessible through the opening, wherein the inflatable membrane has a textured exterior including one or more features to permit passage of air around an exterior of the inflatable membrane from the distal end to the proximal end when the inflatable membrane may be inflated within a passage; a supply of a medium coupled to the interior through the opening; and a three-dimensional scanning system including one or more scanner elements disposed within the interior to capture data from the interior and a processor programmed to calculate a three-dimensional shape of the interior based upon the data.

The device may include a pump configured to controllably deliver the medium into the interior. The pump may be configured to deliver the medium at a controlled pressure. The device may include an illumination source disposed within the interior and positioned to illuminate a surface of the interior. The three-dimensional scanning system may calculate a distance through the medium to a point on the interior using a ratio of two different wavelengths of light. The medium may selectively absorbs one wavelength of light more than another wavelength of light. The medium may include at least one of a liquid, a gas, and a gel.

In another aspect, there is disclosed herein a device including an inflatable membrane having a proximal end with an opening, a distal end, and an interior accessible through the opening, wherein the inflatable membrane has a vent tube on an exterior including a channel to permit a passage of air through the vent tube from the distal end to the proximal end when the inflatable membrane may be inflated within a passage; a supply of a medium coupled to the interior through the opening; and a three-dimensional scanning system including one or more scanner elements disposed within the interior to capture data from the interior and a processor programmed to calculate a three-dimensional shape of the interior based upon the data.

The device may include a pump configured to controllably deliver the medium into the interior. The pump may be configured to deliver the medium at a controlled pressure. The device may include an illumination source disposed within the interior and positioned to illuminate a surface of the interior. The three-dimensional scanning system may calculate a distance through the medium to a point on the interior using a ratio of two different wavelengths of light. The medium may selectively absorb one wavelength of light more than another wavelength of light. The medium may include at least one of a liquid, a gas, and a gel.

In another aspect, there is disclosed herein a device including an inflatable membrane having a proximal end with an opening, a distal end, and an interior accessible through the opening, wherein the inflatable membrane has a lubricant on an exterior surface thereof to facilitate movement of the inflatable membrane along a surface of a cavity while the inflatable membrane may be inflating within the cavity; a supply of a medium coupled to the interior through the opening; and a three-dimensional scanning system including one or more scanner elements disposed within the interior to capture data from the interior and a processor programmed to calculate a three-dimensional shape of the interior based upon the data.

The device may include a pump configured to controllably deliver the medium into the interior. The pump may be configured to deliver the medium at a controlled pressure. The device may include an illumination source disposed within the interior and positioned to illuminate a surface of the interior. The three-dimensional scanning system may calculate a distance through the medium to a point on the interior using a ratio of two different wavelengths of light. The medium may selectively absorb one wavelength of light more than another wavelength of light.

BRIEF DESCRIPTION OF THE FIGURES

The invention and the following detailed description of certain embodiments thereof may be understood by reference to the following figures.

DETAILED DESCRIPTION

Disclosed herein are various modifications to inflatable membranes such as balloons for use in three-dimensional imaging systems, and more particularly, modifications for use with three-dimensional imaging systems designed for imaging of interior spaces. While emphasis in the following description is on imaging of the human ear canal, it will be understood that the principles of the invention have broader applicability, and may be usefully employed for imaging of any other interior spaces including organs such as the bladder or stomach, and any other non-biological cavities where accurate three-dimensional data is desired.

Throughout this disclosure, various terms of quantitative and qualitative description are used. These terms are not intended to assert strict numerical boundaries on the features described, but rather should be interpreted to permit some variability. Thus for example where a medium is described as being transparent at a particular wavelength, this should be understood to mean substantially transparent or sufficiently transparent to permit measurements yielding accurate thickness calculations, rather than absolutely transparent at the limits of measurement or human perception. Similarly, where a target surface is described as having uniform color or a dye is described as fluorescing at a particular wavelength, this should not be interpreted to exclude the variability typical of any conventional material or manufacturing process. Thus in the following description, all descriptive terms and numerical values should be interpreted as broadly as the nature of the invention permits, and will be understood by one of ordinary skill in the art to contemplate a range of variability consistent with proper operation of the inventive concepts disclosed herein, unless a different meaning is explicitly provided or otherwise clear from the context.

In the following description, the term wavelength is used to describe a characteristic of light or other electromagnetic energy. It will be understood that the term wavelength may refer to a specific wavelength, such as where the description refers to a center frequency or a limit or boundary for a range of frequencies. The term may also or instead refer generally to a band of wavelengths, such as where a wavelength is specified for a sensor, pixel, or the like. Thus in general the term wavelength as used herein should be understood to refer to either or both of a specific wavelength and a range of wavelengths unless a more specific meaning is provided or otherwise clear from the context.

All documents mentioned herein are hereby incorporated by reference in their entirety. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context.

Although the following disclosure includes example embodiments, these examples are provided for illustration only and are not intended in a limiting sense. All variations, modifications, extensions, applications, combinations of components, and the like as would be apparent to one of ordinary skill in the art are intended to fall within the scope of this disclosure.

Figure 1:
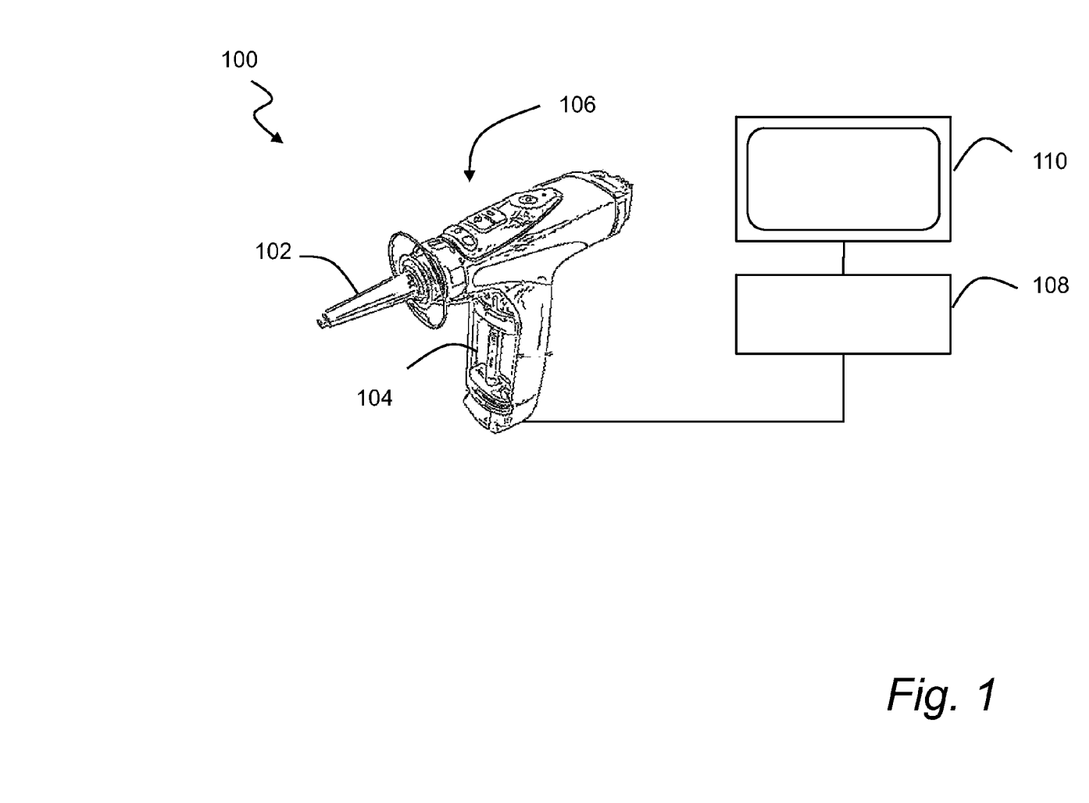
FIG. 1 illustrates an imaging system including an inflatable membrane.

FIG. 1 illustrates an imaging system including an inflatable membrane. In general, the system 100 may include an inflatable membrane 102, a supply of a medium 104, and a three-dimensional scanner 106.

Figure 2:
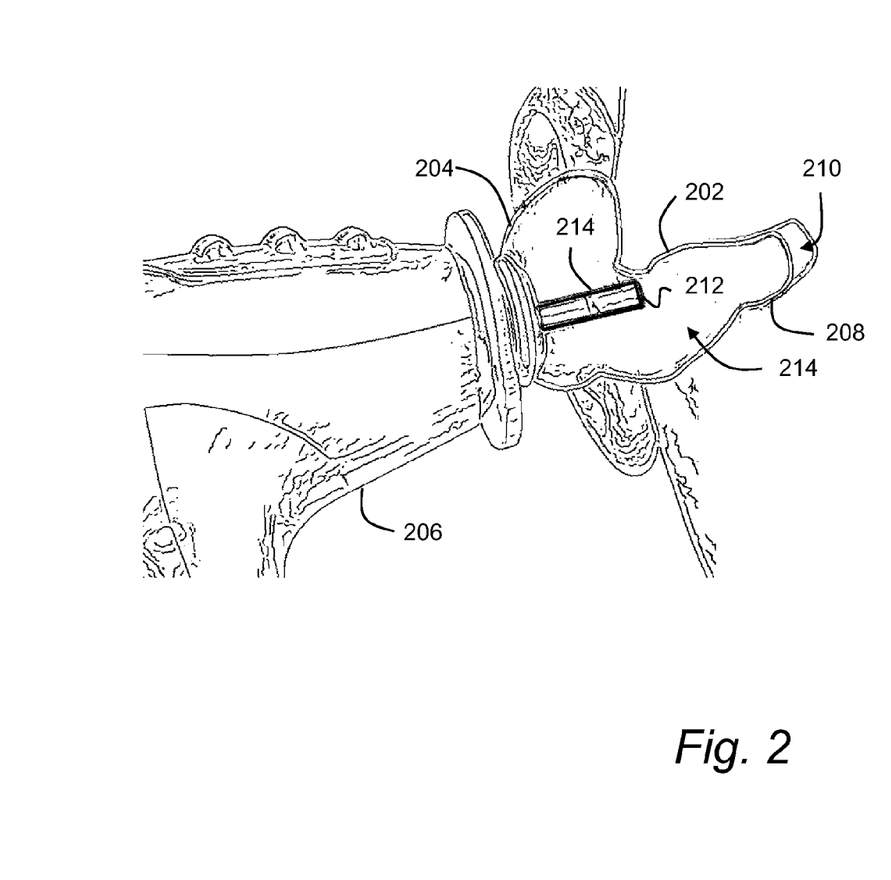
FIG. 2 shows a scanner with an inflatable membrane placed for use in an ear canal.

The system 100 may have a variety of form factors. For example, the system 100 may include a standalone handheld enclosure including a processor and other hardware for independent operation as a handheld scanner. The system 100 may also or instead include a handheld probe coupled to a computer or other computing device as shown in FIG. 2. The computing device 108 may include a processor programmed to receive data from a sensor within the inflatable membrane and calculate three-dimensional data from the data, and to perform other functions associated with the imaging systems described herein. The computing device 108 may also include a display 110 for displaying three-dimensional images, as well as providing a user interface for operation of the system 100 and so forth. It will be understood that in general, processing functions associated with the system 100 may be performed by the computing device 108, the handheld probe, or some combination of these.

The inflatable membrane 102 may in general be any inflatable membrane suitable for insertion into a cavity and inflation therein. The inflatable membrane 102 may, for example, be formed of an elastic material that permits the inflatable membrane 102 to conform to such a cavity as it expands. For ear canal imaging in particular, the inflatable membrane 102 may have a gross geometry, i.e., overall inflated three-dimensional shape and size, generally adapted to any cavity in which the inflatable membrane 102 is to be inserted for use. For example, the inflatable membrane 102 may be shaped and sized to have a gross geometry corresponding to a human ear canal. The inflatable membrane 102 may instead be shaped and sized to have a gross geometry corresponding to other human anatomy such as a stomach, an esophagus, a bladder, and so forth. It will be understood that in some implementations, this correspondence may include some degree of over-sizing so that the inflatable membrane 102 can be inflated to fully occupy a cavity and press against interior walls of the cavity, e.g., with a predetermined or measured pressure. Alternatively, in some implementations, this correspondence may include some degree of under-sizing, to mitigate the potential of the inflatable membrane 102 folding over itself during deployment.

The medium 104 may be any liquid, gas, gel, or combination of the foregoing, and may include additives dissolved into or suspended in the medium 104 as appropriate to a particular imaging technology. For example, the medium 104 may selectively absorb one wavelength of light more than another wavelength of light, such as with the use of a colored dye or other wavelength-selective additive. The medium 104 may also or instead include luminescent or fluorescent substances used by the three-dimensional scanner 106 to determine shape or distance in three-dimensions.

The three-dimensional scanner 106 may use any suitable techniques for recovering three-dimensional data from the interior of the inflatable membrane 102. A variety of useful techniques are described by way of examples in U.S. Pat. No. 8,107,086 for recovering three-dimensional data from a single frame of image data; however, numerous other useful techniques may be adapted to imaging as contemplated herein, including without limitation techniques using structured light, laser line scanning, confocal imaging, shape from motion, plenoptic light fields, and so forth. All such techniques that are suitable for capturing the three-dimensional shape of the interior of an inflatable membrane may be used as the three-dimensional scanner 106 described herein.

A display 110 may be provided for viewing two-dimensional images from the system 100, reconstructed three-dimensional images from the system 100, a user interface for controlling the system 100, and so forth.

FIG. 2 shows a scanner with an inflatable membrane placed for use in an ear canal. The inflatable membrane 202 includes a proximal end 204 nearer to a handheld probe 206 for using the inflatable membrane 202, and a distal end 208 away from the handheld probe 206 for insertion into an ear canal 210. In use, the inflatable membrane may be inserted into the ear canal 210, and then inflated with medium from an external supply, e.g., from a reservoir and pump within the handheld probe 206.

The inflatable membrane 202 may generally include one or more scanner elements 212 for a three-dimensional scanning system disposed within an interior 214 of the inflatable membrane 202 to capture data from the interior 214. The scanning elements 212 may be fixed to a rigid rod 214 or the like to facilitate steering of a field of view, or otherwise disposed in any manner and at any location within the inflatable membrane 202.

It will be noted that a three-dimensional scanner may in general include a variety of sensors and other components, along with a processor, light sources, optical components, transducers (e.g., for ultrasound) and so forth, all depending upon the particular three-dimensional scanning technique deployed, and that such components may be distributed in various ways inside and outside of the inflatable membrane 202. In general, for the uses contemplated herein, such a system includes at least one "scanner element" disposed within the inflatable membrane 102. This may be a digital component such as a charge-coupled device, complementary metal oxide semiconductor device, or other light sensor positioned within the inflatable membrane 102 and coupled to external components such as a processor. This may also or instead include an optical component such as one or more fibers, lenses and so forth that optically transfer images to an external acquisition and processing system. This may also or instead include a transducer such as an ultrasonic transducer or any other combination of active and passive elements used to acquire three-dimensional information non-optically. Thus it will be appreciated that the term scanner element is intended to be used broadly, and is not intended to imply any particular type of scanner element, scanner, or scanning technology, except inasmuch as such a scanner element is positioned within the inflatable membrane 102 to acquire data from the interior 214 for three-dimensional processing.

Figure 3:
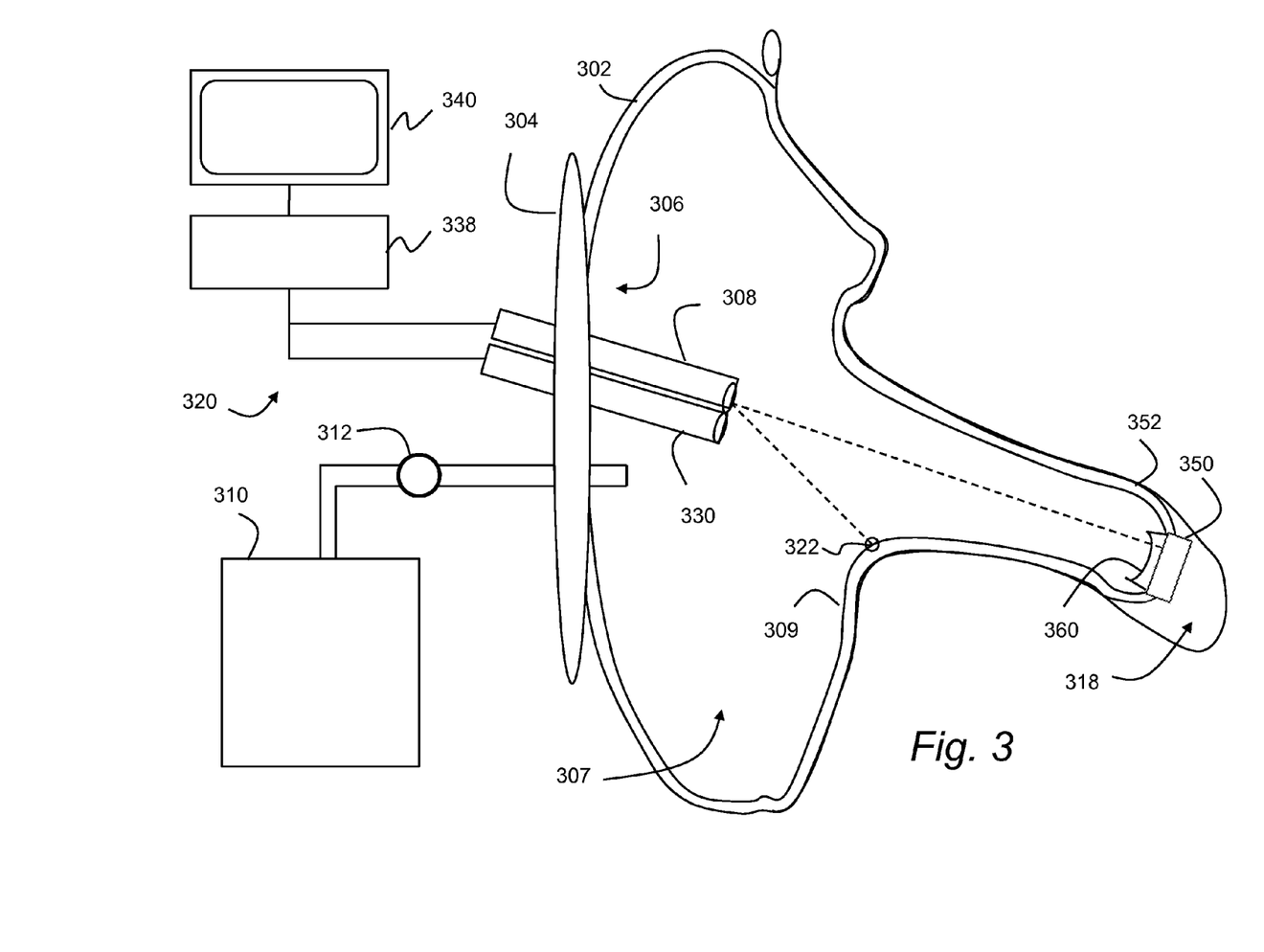
FIG. 3 shows a scanner with an inflatable membrane placed for use in an ear canal.

FIG. 3 shows a scanner with an inflatable membrane placed for use in an ear canal. The inflatable membrane 302 may in general be as described above.

A backing plate 304 may be provided to couple the inflatable membrane 302 to a handheld probe (not shown) or the like to permit positioning and other manipulation of the inflatable membrane 302 and associated hardware.

The proximal end of the inflatable membrane 302 may include an opening 306 so that an interior 307 of the inflatable membrane 302 is accessible through the opening 306. In this manner, the opening 306 may provide a port for accessing components within the interior such as one or more scanner elements 308. A supply of medium 310 may be coupled (e.g. through a pump 312) to the interior 307 through the opening 306 as well. The pump 312, which may be a manual, automatic, or semi-automatic pump, may be configured to deliver the medium 310 at a controlled pressure or volume such as to inflate the inflatable membrane 302 to a predetermined pressure or volume within the ear canal 318.

A three-dimensional scanning system 320 including the scanner element(s) 308, along with a computer or other computing device having a processor 338, a display 340, and so forth, may in general acquire data from the scanner element(s) 308. The processor may be programmed to calculate a three-dimensional shape of the interior 307 based upon the data. As noted above, this may employ any of a variety of three-dimensional processing techniques known in the art. For example, using the techniques disclosed in U.S. Pat. No. 8,107,086, the three-dimensional scanning system 320 may calculate a distance through the medium 310 (which is used to inflate the inflatable membrane 302) to a point 322 on the interior 307, or more specifically on the surface 309 of the interior 307, using a ratio of intensity of two different wavelengths of light. By combining this information for a number of points with information about the direction of such points from the scanner element 308, a three-dimensional image of the interior 307 can be reconstructed using simple geometry.

The scanning system 320 may include an illumination source 330 disposed within the interior 307 and positioned to illuminate a surface 309 of the interior 307. The illumination source 330 may provide any type of illumination such as white light to permit viewing of images on a display 340 or the like, or any narrow wavelength, range of wavelengths, or set of ranges of wavelengths suitable to a particular imaging technology being used.

In general, the inflatable membrane 302, which may be any of the inflatable membranes described above, may have a circular cross section, or any other suitable cross-sectional shape, such as an oval cross section, or a cross section that varies in shape along its length.

The inflatable membrane 302 may also or instead have an inflation characteristic that is non-uniform. As used herein, the term inflation characteristic is intended to refer to any characteristic or property of the inflatable membrane 302, or materials disposed on or in the material of the inflatable membrane 302, that affects the manner in which the inflatable membrane 302 inflates under pressurization. For example, the inflatable membrane 302 may have an inflation characteristic such as a thickness or hardness that varies about the surface of the inflatable membrane 302, thus causing the inflatable membrane to inflate in a predetermined manner when pressurized. For example, when inflating in the ear canal 318, it may be desirable for the inflatable membrane 302 to inflate from the distal end (away from the opening 306) to the proximal end in order to reduce or mitigate pressurization of the ear canal 318 during inflation. By forming a seal within the ear canal 318 at the distal end first, this can also mitigate trapping of air bubbles or the like along the contact surface between the inflatable membrane 302 and the ear canal 318. To achieve this end, the proximal end may be formed of a thicker layer or a harder material than the distal end so that the predetermined manner of inflation includes inflation at the distal end before inflation at the proximal end.

In another aspect, the inflatable membrane 302 may be formed of an elastic material that is exercised (e.g. at the distal end) by stretching, straining, heating, or other manipulation to alter elasticity, thus imparting the desired inflation characteristic (e.g., a localized, reduced spring constant of an elastic material) to the inflatable membrane 302 for inflation in a predetermined manner (e.g., the exercised regions can inflate before unexercised regions). The inflatable membrane 302 may be exercised in this manner immediately prior to use, or at any other time prior to use such as prior to packaging for shipping to an end user.

In some implementations, the thickness of the inflatable membrane 302 may accounted for in obtaining the three-dimensional image data. The thickness of the inflatable membrane 302 may be determined in any manner. For example, the thickness of the inflatable membrane 302 may be known or assumed a priori. However, the thickness of the inflatable membrane 302 may change in unpredictable ways after it is inflated in a cavity of unknown dimensions. To account for such changes, a number of other techniques are possible.

For example, the rough geometry of the cavity can be assumed in advance to be a cylinder, sphere, or other convenient shape. The increase in volume of the inflatable membrane after deployment can be used, in combination with the assumed geometry, to determine an average decrease in the thickness of the membrane 302. This average decrease can then be assumed to uniformly take place over the entire surface the membrane 302.

In another example, the relative positions of fiducials (described below) on the inflatable membrane 302 can be compared in a deployed state vs. an undeployed state or other state in which the thickness of the inflatable membrane is known. This comparison, in combination with known material properties of the inflatable membrane 302 (compressibility, Poisson ratio, etc.) can be used to model the potentially varying thickness of the inflatable membrane. This has the advantage of accounting for potentially non-uniform variation of thickness the membrane 302 experiences in its deployed state.

For optically based three-dimensional imaging techniques, the inflatable membrane may include an optical coating on the interior 309 thereof selected to improve performance of the three-dimensional scanning system. For example, the optical coating may include a matte finish to prevent light scattering and resulting imaging artifacts that might otherwise be caused by a glossy surfaces. The optical coating may also or instead include a fluorescent dye. The optically coating may also or instead include an optically absorptive coating, such as a black or other highly absorptive pigment or combination of pigments. In another aspect, the optical coating may include a predetermined color, which, as described in U.S. Pat. No. 8,107,086, for example, may be used in combination with a medium that differentially absorbs different wavelengths to resolve three-dimensional data. Particular colors may provide other advantages in varying conditions, and no particular predetermined color is intended to be required by the foregoing description.

An optical material may be disposed within a wall of the inflatable membrane to similar affect. The optical material may for example include a fluorescent dye, a luminescent material, a black material, a pigment or the like. The optical material may be distributed throughout the entire inflatable membrane 302, or in a pattern to form one or more fiducials for the three-dimensional scanning system.

Where the scanner element 308 is an optical sensor such as an active (e.g., charge-coupled device) or passive (e.g., lens or fiber optic tip) imaging device, the optical sensor may usefully include a coating having an index of refraction matched to the index of refraction of the medium 310. In this manner, optical distortion can be mitigated at the interface between the optical sensor and the medium.

In another aspect, the inflatable membrane 302 may include a window 350 of transparent material in the distal end 352 providing a view from the interior 307 of the inflatable membrane to an exterior of the inflatable membrane 302 such as the ear canal 318. This can provide visibility for positioning of the inflatable membrane 302, such as to ensure that the inflatable membrane 302 is inserted sufficiently deep into the ear canal 318, or to avoid collisions with sensitive tissue such as the tympanic membrane. In such embodiments, the scanner element 308 may include a camera or other imaging device oriented toward the window 350, and the display 340 may be coupled to the camera by the scanning system 320 in order to display video images from the camera. The camera or other imaging device may have an optical coating with an index of refraction matched to the index of refraction of the medium 310.

At certain times, such as during insertion of the inflatable membrane 302 into the ear canal 318, it may be desirable to have a view from the distal end 352 of the inflatable membrane 302 to facilitate manual navigation of the tip. To facilitate this navigation, the distal end 352 may include a fixture in the interior 307 shaped and sized to receive an imaging device such as an endoscope or an otoscope, and to align the imaging device to the window 350 in order to provide a view of the exterior through the window 350 with the imaging device. The imaging device may be the scanner element 308, or may be an additional imaging device separate and independent from the scanning system 320. The display 340 may be coupled to the imaging device and configured to display video images therefrom. The imaging device may have an optical coating having an index of refraction matched to the medium 310.

Figure 4:
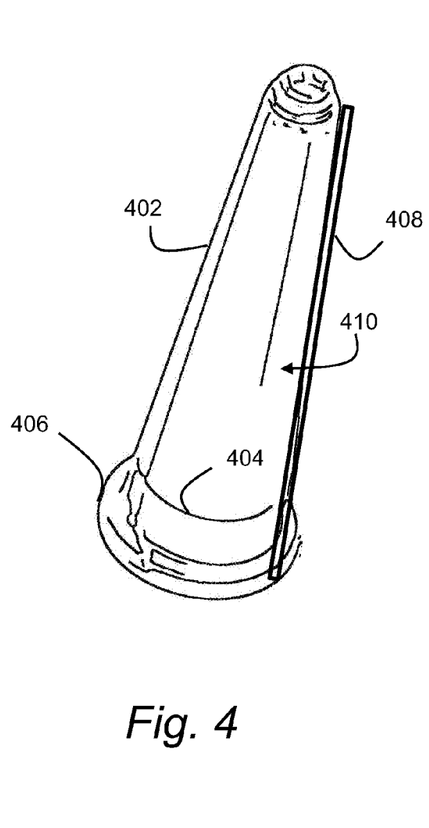
FIG. 4 shows an inflatable membrane with a substantially conical profile.

FIG. 4 shows an inflatable membrane 402 with a substantially conical profile. The inflatable membrane 402 may be used with any of the systems described above. The inflatable membrane 402 may include a reinforcing sheath 404 of a second elastic material or a non-elastic band or the like about a portion of the inflatable membrane 402 to impart a non-uniform inflation characteristic to the inflatable membrane 402. That is, by reinforcing one or more regions of the inflatable membrane 402, the reinforced regions will tend to inflate after regions without such reinforcement. The sheath 404 may be adhered to the inflatable membrane 402, and/or may wrap fully around the inflatable membrane 402. The sheath 404 may be disposed near the proximal end 406 of the inflatable membrane 402, or at any other suitable location(s) according to the predetermined manner of inflation that is intended.

In one aspect, the inflatable membrane 402 may include a vent tube 408 on an exterior 410 thereof, the vent tube 408 including a channel to permit a passage of air through the vent tube 408 from the distal end to the proximal end 406 when the inflatable membrane 402 is inflated within a passage such as an ear canal. In this manner, if the membrane inflates to the walls of a cavity to seal in a chamber at the distal end, air within the chamber can remain at an ambient pressure even as the chamber volume is reduced by expansion of the inflatable membrane 402 toward the distal end.

In another aspect, a lubricant may be disposed on the exterior 410 surface of the inflatable membrane 402 to facilitate movement of the inflatable membrane 402 along a surface of a cavity while the inflatable membrane 402 is inflating within the cavity. This may advantageously avoid frictionally imposed distortions in the expansion of the inflatable membrane 402 so that the inflatable membrane 402 can fully expand along any adjacent surfaces of the cavity.

Figure 5:
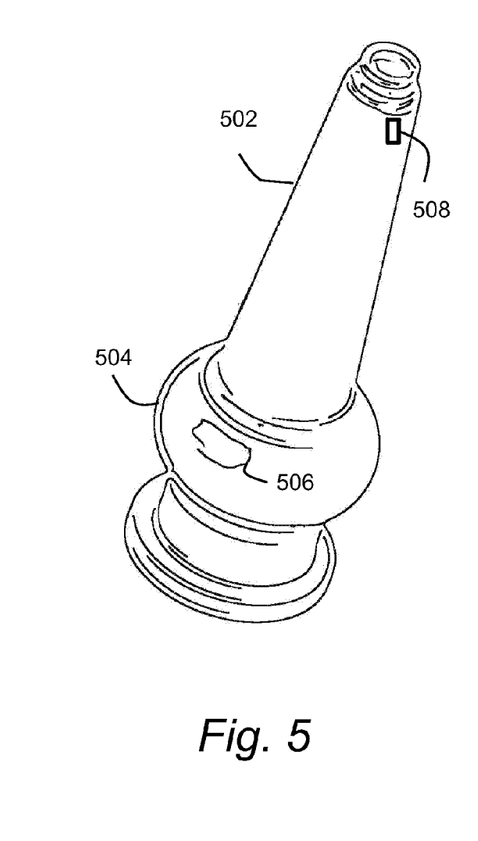
FIG. 5 shows an inflatable membrane.

FIG. 5 shows an inflatable membrane. The inflatable membrane 502 may be used with any of the systems described above. The inflatable membrane 502 may include a bulbous region 504 to form a seal within a cavity, or to accommodate the gross geometry of a cavity such as the ear canal. A pattern 506 of relatively inelastic material may be disposed on a portion of the inflatable membrane, which may provide an inflation characteristic (inelasticity) in the area of the pattern 506 to control the manner in which the inflatable membrane 502 inflates. The pattern 506 may include any size, shape, and number of patterns suitable for controlling inflation of the inflatable membrane 502. For example, the pattern 506 may include circumferential bands about the inflatable membrane 502 or lateral bands at various locations to urge a curved manner of inflation.

More generally, a variety of useful coatings to the exterior may be provided. Pad printing (e.g., 2d image onto 3d surface) or the like may be employed, for example to print fiducials, nonstretching dots or lines, or patterns that reduce reflections on the interior surface of the inflatable membrane. Pad printing may also usefully be employed to reduce elasticity of the inflatable membrane in certain regions, so that certain portions of the inflatable membrane 502 inflate before others, e.g., under lower pressure. This technique may be used, for example to print bands about the inflatable membrane 502 that encourage a tip-to-base inflation.

In one aspect, the inflatable membrane 502 may be instrumented with a sensor such as a proximity sensor 508. The proximity sensor 508 may be configured to provide a signal indicative of a proximity of the distal end to an external object such as an eardrum. The proximity sensor 508 may be wired or wireless, and may be disposed on an interior or an exterior of the inflatable membrane 502. The proximity sensor 508 may include an infrared source/detector, an ultrasonic transducer, or any other device(s) suitable for measuring distance or otherwise detecting proximity. A processor of a three-dimensional scanning system may receive a signal from the proximity sensor 508 and generate an alert under one or more predetermined conditions, e.g., when a collision of the distal end of the inflatable membrane 502 with a wall of a cavity is imminent. The alert may activate an audible alarm, a visual alarm, a tactile alarm, or the like. The alert may also or instead, trigger other actions such as pausing inflation of the inflatable membrane 502.

Figure 6:
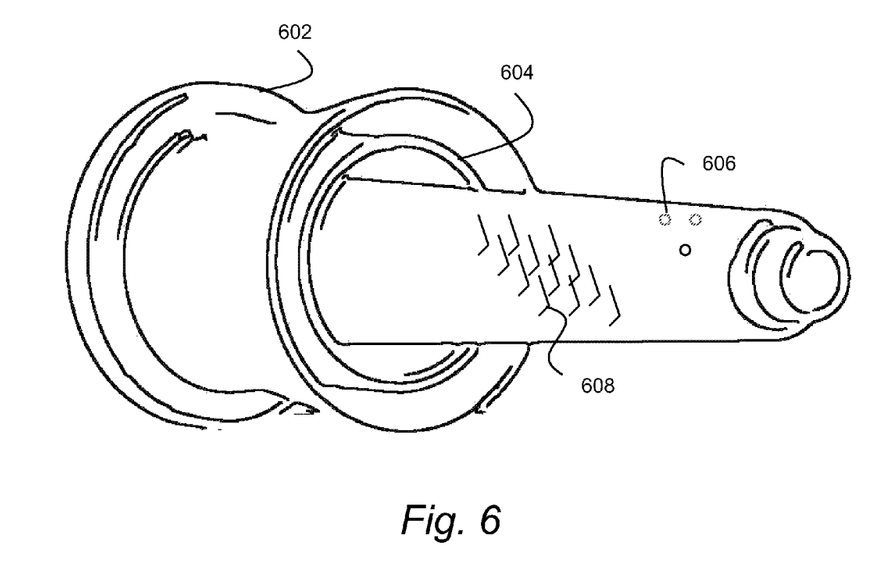
FIG. 6 shows an inflatable membrane.

FIG. 6 shows an inflatable membrane. The inflatable membrane 602 may be used with any of the systems described above, and may include an inflation characteristic for the inflatable membrane 602 to inflate in a predetermined manner. In one aspect, the inflation characteristic may include a bellows 604 formed into a portion of the inflatable membrane, or any other shape or combination of shapes to encourage a predetermined inflation pattern.

The inflatable membrane 602 may include one or more fiducials 606 disposed on the interior thereof. The fiducials 606 may be used by a processor of the three-dimensional scanning system to calculate three-dimensional shape. The use of fiducials is well known in three-dimensional processing arts, and is not described in detail here except to generally note that recognizable features can assist in resolving particular locations within an image and/or across multiple images to facilitate more efficient processing. The one or more fiducials 606 may for example be used to register multiple frames of image data acquired from the scanner element(s) in order to provide a single three-dimensional model from multiple images. The fiducials 606 may include predetermined patterns such as cross-hairs, circles, squares, lines, or any other patterns, and combinations of the foregoing, printed on the interior of the inflatable membrane 602. The fiducials 606 may also or instead include any such pattern(s) embedded into a material of the inflatable membrane during fabrication. In another aspect, the fiducials 606 may include predetermined three-dimensional shapes such as ridges or hemispheres on the interior of the inflatable membrane 602.

The inflatable membrane 602 may include a textured exterior 608 including one or more features to permit passage of air around an exterior of the inflatable membrane from the distal end to the proximal end when the inflatable membrane is inflated within a passage. The textured exterior 608 may include bumps, ridges, or any other features to create intermittent spacing between the inflatable membrane 602 and a wall of a cavity in which the inflatable membrane 602 is inflated.

It will be appreciated that the above computing devices and processors may be realized in hardware, software, or any combination of these suitable for the control, data acquisition, and data processing described herein. This includes realization in one or more microprocessors, microcontrollers, embedded microcontrollers, programmable digital signal processors or other programmable devices, along with internal and/or external memory. This may also, or instead, include one or more application specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. At the same time, processing may be distributed across devices such as a camera and/or computer and/or server or other remote processing resource in a number of ways, or all of the functionality may be integrated into a dedicated, standalone device. All such permutations and combinations are intended to fall within the scope of the present disclosure.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

What is claimed is:

1. A device comprising:
    an inflatable membrane having a proximal end with an opening, a distal end disposed away from the opening, and an interior accessible through the opening, wherein the inflatable membrane has an inflation characteristic that is non-uniform, thereby causing the membrane to inflate in a predetermined manner, the predetermined manner including inflation at the distal end before inflation at the proximal end;
    a supply of a medium coupled to the interior through the opening; and
    a three-dimensional scanning system including at least one scanner element disposed within the interior to capture data from the interior and a processor programmed to calculate a three-dimensional shape of the interior based upon the data.

2. The device of claim 1 further comprising a pump configured to controllably deliver the medium into the interior.

3. The device of claim 2 wherein the pump is configured to deliver the medium at a controlled pressure.

4. The device of claim 1 further comprising an illumination source disposed within the interior and positioned to illuminate a surface of the interior.

5. The device of claim 4 wherein the three-dimensional scanning system calculates a distance through the medium to a point on the interior using a ratio of intensity of two different wavelengths of light.

6. The device of claim 1 wherein the medium selectively absorbs one wavelength of light more than another wavelength of light.

7. The device of claim 1 wherein the medium includes at least one of a liquid, a gas, and a gel.

8. The device of claim 1 wherein the inflatable membrane has a gross geometry corresponding to a human ear canal.

9. The device of claim 1 wherein the inflatable membrane has a gross geometry corresponding to human anatomy selected from a group consisting of a stomach, an esophagus, and a bladder.

10. The device of claim 1 wherein the inflation characteristic includes a thickness of the inflatable membrane.

11. The device of claim 1 wherein the inflation characteristic includes a hardness of the inflatable membrane.

12. The device of claim 1 further comprising a reinforcing sheath about a portion of the inflatable membrane to impart the non-uniform inflation characteristic to the inflatable membrane.

13. The device of claim 12 wherein the sheath is disposed near the proximal end of the inflatable membrane.

14. The device of claim 1 wherein the inflation characteristic includes a pattern of relatively inelastic material disposed on a portion of the inflatable membrane.

15. The device of claim 1 wherein the inflation characteristic includes a bellows formed into a portion of the inflatable membrane.

16. The device of claim 1 wherein a portion of the inflatable membrane is exercised prior to use to alter an elasticity of the portion, thereby imparting the inflation characteristic to the inflatable membrane.

17. The device of claim 1 wherein the inflatable membrane has an oval cross section.

18. The device of claim 1 wherein the inflatable membrane has a circular cross section.

19. The device of claim 1 wherein the inflatable membrane is formed of an elastic material.

* * * * *